United States Patent
Hoffmann et al.

(10) Patent No.: US 9,409,881 B2
(45) Date of Patent: Aug. 9, 2016

(54) HERBICIDALLY ACTIVE 6'-PHENYL-2,2'-BIPYRIDINE-3-CARBOXYLIC ACID DERIVATIVES

(71) Applicant: BAYER CROPSCIENCE AG, Monheim (DE)

(72) Inventors: Michael Gerhard Hoffmann, Floersheim (DE); Uwe Doeller, Rodgau (DE); Marco Bruenjes, Hattersheim am Main (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE)

(73) Assignee: Bayer CropScience AG, Monheim (AG)

( * ) Notice: Subject to any disclaimer, the term of this patent is extended or adjusted under 35 U.S.C. 154(b) by 0 days.

(21) Appl. No.: 14/418,469

(22) PCT Filed: Aug. 2, 2013

(86) PCT No.: PCT/EP2013/066334
§ 371 (c)(1),
(2) Date: Jan. 30, 2015

(87) PCT Pub. No.: WO2014/023670
PCT Pub. Date: Feb. 13, 2014

(65) Prior Publication Data
US 2015/0307470 A1   Oct. 29, 2015

(30) Foreign Application Priority Data
Aug. 7, 2012 (EP) .................. 12179518

(51) Int. Cl.
*C07D 401/04* (2006.01)
*A01N 43/40* (2006.01)
(52) U.S. Cl.
CPC ............. *C07D 401/04* (2013.01); *A01N 43/40* (2013.01)

(58) Field of Classification Search
CPC ....................................... C07D 401/04
USPC .................. 546/257, 258; 514/334
See application file for complete search history.

(56) References Cited

U.S. PATENT DOCUMENTS 4,752,324 A    6/1988  Thomas et al.

FOREIGN PATENT DOCUMENTS

EP    0222254 A2    5/1987
WO    9519358 A1    7/1995

OTHER PUBLICATIONS

International Search Report from corresponding PCT/EP2013/066334, mailed Sep. 4, 2013.
Bijeire et al., "A Total Synthesis of Subarine, a Marine Alkaloid Related to the Pyridoacridine Family", European Journal of Organic Chemistry, Bd. 2004, Nr. 9, May 1, 20014, pp. 1891-1893, XP055039082.

*Primary Examiner* — Patricia L Morris
(74) *Attorney, Agent, or Firm* — McBee Moore Woodward Vanik IP, LLC

(57) ABSTRACT

There are described 6'-phenyl-2,2'-bipyridine-3-carboxylic acid derivatives of the general formula (I) as herbicides.

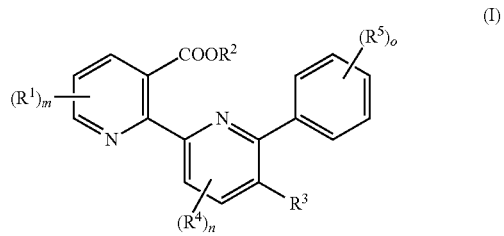

In this formula (I), $R^1$ to $R^5$ are radicals such as hydrogen, organic radicals such as alkyl, and other radicals such as halogen, nitro, cyano and formyl.

11 Claims, No Drawings

HERBICIDALLY ACTIVE 6'-PHENYL-2,2'-BIPYRIDINE-3-CARBOXYLIC ACID DERIVATIVES

CROSS REFERENCE TO RELATED APPLICATIONS

This application is a §371 National Stage Application of PCT/EP2013/066334, filed Aug. 2, 2013, which claims priority to EP 12179518.1, filed Aug. 7, 2012.

BACKGROUND

Field of the Invention

The invention relates to the technical field of herbicides, especially that of herbicides for the selective control of broad-leaved weeds and weed grasses in crops of useful plants.

WO 95/19358 A1 discloses herbicidally active aryl- and heteroarylpyrimidines which have a nicotinic acid radical attached to them. However, frequently, the compounds known from this publication have insufficient herbicidal activity and/or an insufficient compatibility with crop plants. Accordingly, it is an object of the present invention to provide further herbicidally active compounds. It has now been found that particular 6'-phenyl-2,2'-bipyridine-3-carboxylic acid derivatives are particularly suitable as herbicides.

A subject-matter of the present invention are 6'-phenyl-2,2'-bipyridine-3-carboxylic acid derivatives of the formula (I), their N oxides and their salts

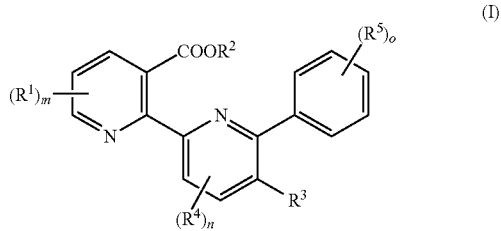

in which $R^1$, $R^4$ and $R^5$ independently of one another are nitro, halogen, cyano, formyl, rhodano, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^7$, $COOR^7$, $N(R^7)_2$, $NR^7COOR^6$, $C(O)N(R^7)_2$, $NR^7C(O)N(R^7)_2$, $OC(O)N(R^7)_2$, $C(O)NR^7OR^7$, $OR^7$, $OCOR^7$, $OSO_2R^6$, $S(O)_wR^6$, $SO_2OR^6$, $SO_2N(R^7)_2$, $NR^7SO_2R^6$, $NR^7OR^7$, $(C_1\text{-}C_6)$-alkyl-$S(O)_wR^6$, $(C_1\text{-}C_6)$-alkyl-$OR^7$, $(C_1\text{-}C_6)$-alkyl-$OSO_2R^6$, $(C_1\text{-}C_6)$-alkyl-$CO_2R^7$, $(C_1\text{-}C_6)$-alkyl-$SO_2OR^6$, $(C_1\text{-}C_6)$-alkyl-$CON(R^7)_2$, $(C_1\text{-}C_6)$-alkyl-$SO_2N(R^7)_2$, $(C_1\text{-}C_6)$-alkyl-$NR^7COR^7$, $(C_1\text{-}C_6)$-alkyl-$NR^7SO_2R^6$, $P(O)(OR^7)_2$, $CH_2P(O)(OR^7)_2$, heteroaryl, heterocyclyl, $(C_1\text{-}C_6)$-alkyl-heteroaryl or $(C_1\text{-}C_6)$-alkylheterocyclyl, where the four last-mentioned radicals are in each case substituted by s radicals selected from the group consisting of halogen, nitro, cyano, $(C_1\text{-}C_6)$-alkyl, halo-$(C_1\text{-}C_6)$-alkyl, $S(O)_w$—$(C_1\text{-}C_6)$-alkyl, $(C_1\text{-}C_6)$-alkoxy and halogen-$(C_1\text{-}C_6)$-alkoxy, and where heterocyclyl has n oxo groups attached to it, $R^2$ is hydrogen, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl or halo-$(C_3\text{-}C_6)$-cycloalkyl-$(C_1\text{-}C_6)$-alkyl, $R^3$ is hydrogen, halogen, $(C_1\text{-}C_6)$-alkyl, halo-$(C_1\text{-}C_6)$-alkyl, $(C_2\text{-}C_6)$-alkenyl, halogen-$(C_2\text{-}C_6)$-alkenyl, $(C_2\text{-}C_6)$-alkynyl, halogen-$(C_2\text{-}C_6)$-alkynyl, $(C_3\text{-}C_6)$-cycloalkyl or halogen-$(C_3\text{-}C_6)$-cycloalkyl, $R^6$ is $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_4\text{-}C_8)$-cycloalkenyl, halo-$(C_3\text{-}C_6)$-cycloalkenyl, $(C_3\text{-}C_6)$-cycloalkyl-$(C_1\text{-}C_6)$-alkyl or halo-$(C_3\text{-}C_6)$-cycloalkyl-$(C_1\text{-}C_6)$-alkyl, $R^7$ is hydrogen, $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-halocycloalkyl, $(C_4\text{-}C_8)$-cycloalkenyl, $(C_3\text{-}C_6)$-halocycloalkenyl, $(C_3\text{-}C_6)$-cycloalkyl-$(C_1\text{-}C_6)$-alkyl, or $(C_3\text{-}C_6)$halocycloalkyl-$(C_1\text{-}C_6)$-alkyl, n is 0, 1 or 2,
m is 0, 1, 2 or 3,
o is 0, 1, 2, 3, 4 or 5,
s is 0, 1, 2 or 3,
w is 0, 1 or 2.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, and hexyls, such as n-hexyl, isohexyl, and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl represents a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl represents an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals among those mentioned. This applies analogously to the formation of ring systems by various atoms and elements. At the same time, the scope of the claims shall exclude those compounds known by the person skilled in the art to be chemically unstable under standard conditions.

Depending on the nature of the substituents and the way in which they are attached, the compounds of the general formula (I) may be present as stereoisomers. If, for example, one or more asymmetric carbon atoms are present, enantiomers and diastereomers may occur. Stereoisomers likewise occur when n represents 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all stereoisomers and mixtures thereof which are encompassed by the general formula (I) but not defined specifically. Owing to the oxime ether structure, the compounds according to the invention may also occur as geometric isomers (E/Z isomers). The invention also relates to all E/Z isomers and mixtures thereof which are encompassed by the general formula (I) but not defined specifically.

The compounds of the formula (I) can form salts, in particular in the case that $R^2$ is hydrogen. Salts can be formed by the action of a base on those compounds of the formula (I) which have an acidic hydrogen atom attached to them, for example in the case of R'. Examples of suitable bases are organic amines such as trialkylamines, morpholine, piperidine or pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, in particular alkali metal salts or alkaline-earth metal salts, in particular sodium and potassium salts, or else ammonium salts, salts with organic amines or quaternary ammonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. In such a case, these salts will comprise the conjugated base of the acid as the anion.

Preference is given to compounds of the general formula (I) in which $R^1$, $R^4$ and $R^5$ independently of one another are in each case nitro, halogen, cyano, formyl, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_2$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $COR^7$, $COOR^7$, $N(R^7)_2$, $NR^7COOR^6$, $C(O)N(R^7)_2$, $NR^7C(O)N(R^7)_2$, $OC(O)N(R^7)_2$, $C(O)NR^7OR^7$, $OR^7$, $S(O)_wR^6$, $SO_2OR^6$, $SO_2N(R^7)_2$, $NR^7SO_2R^6$, $(C_1$-$C_6)$-alkyl-$S(O)_wR^6$, $(C_1$-$C_6)$-alkyl-$OR^7$, $(C_1$-$C_6)$-alkyl-$OSO_2R^6$, $(C_1$-$C_6)$-alkyl-$CO_2R^7$, $(C_1$-$C_6)$-alkyl-$SO_2OR^6$, $(C_1$-$C_6)$-alkyl-$CON(R^7)_2$, $(C_1$-$C_6)$-alkyl-$SO_2N(R^7)_2$, $(C_1$-$C_6)$-alkyl-$NR^7COR^7$, $(C_1$-$C_6)$-alkyl-$NR^7SO_2R^6$, $P(O)(OR^7)_2$, $CH_2P(O)(OR^7)_2$, heteroaryl, heterocyclyl, $(C_1$-$C_6)$-alkyl-heteroaryl or $(C_1$-$C_6)$-alkylheterocyclyl, where the four last-mentioned radicals are in each case substituted by s radicals selected from the group consisting of halogen, nitro, cyano, $(C_1$-$C_6)$-alkyl, halo-$(C_1$-$C_6)$-alkyl, $S(O)_w$—$(C_1$-$C_6)$-alkyl, $(C_1$-$C_6)$-alkoxy and halo-$(C_1$-$C_6)$-alkoxy, and where heterocyclyl has n oxo groups attached to it, $R^2$ is hydrogen, $(C_1$-$C_6)$-alkyl, halo-$(C_1$-$C_6)$-alkyl $(C_2$-$C_6)$-alkenyl, $(C_2$-$C_6)$-alkynyl, $(C_3$-$C_6)$-cycloalkyl or $(C_3$-$C_6)$-cycloalkyl-$(C_1$-$C_6)$-alkyl, $R^3$ is hydrogen, halogen, $(C_1$-$C_6)$-alkyl, halo-$(C_1$-$C_6)$-alkyl, $(C_2$-$C_6)$-alkenyl, $(C_2$-$C_6)$-alkynyl or $(C_3$-$C_6)$-cycloalkyl, $R^6$ is $(C_1$-$C_6)$-alkyl, $(C_2$-$C_6)$-alkenyl, $(C_2$-$C_6)$-alkynyl, $(C_3$-$C_6)$-cycloalkyl, $(C_4$-$C_8)$-cycloalkenyl or $(C_3$-$C_6)$-cycloalkyl-$(C_1$-$C_6)$-alkyl, $R^7$ is hydrogen, $(C_1$-$C_6)$-alkyl, $(C_2$-$C_6)$-alkenyl, $(C_2$-$C_6)$-alkynyl, $(C_3$-$C_6)$-cycloalkyl, $(C_4$-$C_8)$-cycloalkenyl or $(C_3$-$C_6)$-cycloalkyl-$(C_1$-$C_6)$-alkyl, n is 0 or 1, m is 0, 1 or 2, o is 0, 1, 2 or 3, s is 0, 1, 2 or 3, w is 0, 1 or 2.

Particular preference is given to compounds of the general formula (I) in which $R^1$, $R^4$ and $R^5$ independently of one another are in each case nitro, halogen, cyano, formyl, $(C_1$-$C_4)$-alkyl, halo-$(C_1$-$C_4)$-alkyl, $(C_2$-$C_6)$-alkenyl, halo-$(C_2$-$C_6)$-alkenyl, $(C_2$-$C_6)$-alkynyl, halo-$(C_2$-$C_6)$-alkynyl, $(C_3$-$C_6)$-cycloalkyl, $(C_3$-$C_6)$-cycloalkyl-$(C_1$-$C_6)$-alkyl, $COR^7$, $COOR^7$, $N(R^7)_2$, $NR^7COOR^6$, $C(O)N(R^7)_2$, $NR^7C(O)N(R^7)_2$, $OC(O)N(R^7)_2$, $C(O)NR^7OR^7$, $OR^7$, $S(O)_wR^6$, $SO_2N(R^7)_2$, $NR^7SO_2R^6$, $(C_1$-$C_6)$-alkyl-$S(O)_wR^6$, $(C_1$-$C_6)$-alkyl-$OR^7$ or $(C_1$-$C_6)$-alkyl-$SO_2N(R^7)_2$, $R^2$ is hydrogen or $(C_1$-$C_6)$-alkyl, $R^3$ is hydrogen, halogen, $(C_1$-$C_6)$-alkyl or halo-$(C_1$-$C_6)$-alkyl, $R^6$ is $(C_1$-$C_6)$-alkyl, $R^7$ is hydrogen or $(C_1$-$C_6)$-alkyl, n is 0 or 1, m is 0 or 1, o is 0, 1, 2 or 3, w is 0, 1 or 2.

In all the formulae specified hereinafter, the substituents and symbols have the same meaning as described in formula (I), unless defined differently.

Compound according to the invention can be prepared for example in the method specified in the diagram hereinbelow.

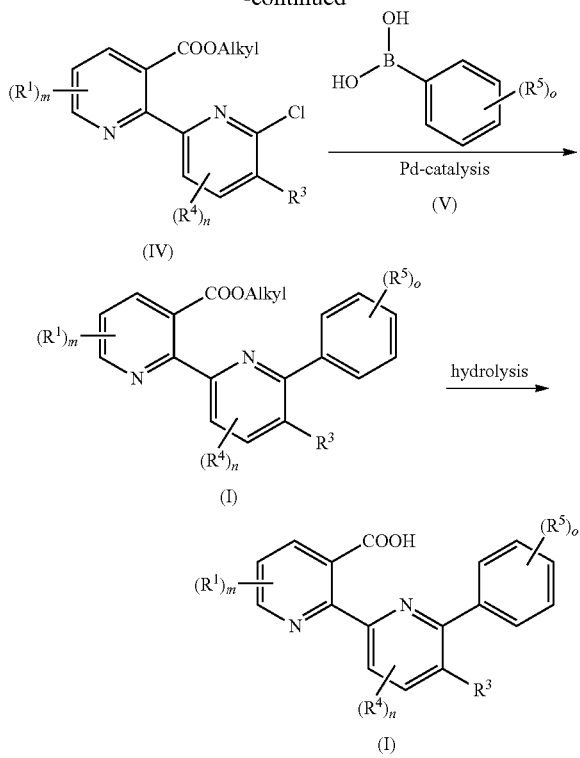

The starting materials used here are either commercially available or can be prepared by simple methods known to the skilled worker, for example as described in Journal of Org. Chemistry, 75(22), 7691; 2010 and Org. Synth. Coll., 1963, 4, 68.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from Perkin Elmar, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the completion of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the methods described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), referred to collectively as "inventive compounds" hereinafter, have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the emergence of the weed seedlings is prevented completely or the weeds grow until they have reached the cotyledon stage, but then they stop growing and ultimately die completely after three to four weeks have passed.

If the active compounds are applied post-emergence to the green parts of the plants, growth stops after the treatment, and the harmful plants remain at the growth stage of the time of application, or they die completely after a certain time, such that competition by the weeds, which is harmful to the crop plants, is thus eliminated very early and in a lasting manner.

Although the inventive compounds have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* will be damaged to a negligible extent only, if at all, depending on the structure of the particular inventive compound and its application rate. For these reasons, the present compounds are very suitable for selective control of unwanted plant growth in plant crops such as agriculturally useful plants or ornamental plants.

In addition, the inventive compounds (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous crops since, for example, this can reduce or completely prevent lodging.

By virtue of their herbicidal and plant-growth-regulating properties, the active compounds can also be used for controlling harmful plants in crops of genetically modified plants or plants modified by conventional mutagenesis. In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. It is preferred to employ the compounds according to the invention as herbicides in crops of useful plants which are resistant, or have been made resistant by recombinant means, to the phytotoxic effects of the herbicides.

Preference is given to the use of the inventive compounds or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other types of vegetable. Preferably, the inventive compounds can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of recombinant modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylureas (EP-A-0257993, U.S. Pat. No. 5,013,659), are resistant, transgenic crop plants, for example cotton, with the ability to produce *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461)

genetically modified plants with reduced photorespiration which feature higher yields and higher stress tolerance (EPA 0305398).

transgenic crop plants which produce pharmaceutically or diagnostically important proteins ("molecular pharming")

transgenic crop plants which feature higher yields or better quality, transgenic crop plants which feature a combination, for example, of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or sequence alteration by recombination of DNA sequences can be introduced into plasmids. With the aid of standard methods, it is possible, for example, to undertake base exchanges, remove part-sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850, Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the inventive active compounds are used in transgenic crops, not only do the effects toward harmful plants which are observed in other crops occur, but often also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of harmful plants in transgenic crop plants.

On account of the herbicidal property of the compounds of the general formula (I), the invention also further provides the use of the inventive compounds of the general formula (I) as herbicides for controlling harmful plants.

The inventive compounds can be applied in the form of wettable powders, emulsifiable concentrates, sprayable solutions, dusting products or granules in the customary formulations. The invention therefore also provides herbicidal and plant-growth-regulating compositions which comprise the inventive compounds.

The inventive compounds can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N. J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active compound with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto adsorptive granular inert material or by applying active compound concentrates to the surface of carriers, such as sand, kaolinites or granular inert material, by means of adhesives, for example polyvinyl alcohol, sodium polyacrylates or else mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations contain generally 0.1 to 99% by weight, especially 0.1 to 95% by weight, of inventive compounds.

In wettable powders, the active compound concentration is, for example, about 10 to 90% by weight, the remainder to 100% by weight consisting of customary formulation constituents. In emulsifiable concentrates, the active compound concentration may be about 1 to 90% and preferably 5 to 80% by weight. Dust-type formulations contain 1 to 30% by weight of active compound, preferably usually 5 to 20% by weight of active compound; sprayable solutions contain about 0.05 to 80% by weight and preferably 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

Active ingredients which can be employed in combination with the compounds according to the invention in mixed formulations or in the tank mix are, for example, known active ingredients which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

The required application rate of the compounds of the formula (I) varies inter alia with the external conditions, including temperature, humidity and the type of herbicide used.

It can vary within wide limits, for example between 0.001 and 1.0 kg/ha or more of active substance, but it is preferably between 0.005 and 750 g/ha.

The examples below illustrate the invention.

A. Chemical Examples

1. Methyl 6'-chloro-2,2'-bipyridine-3-carboxylate (1)

0.49 g (0.70 mmol) of $(Ph_3P)_2PdCl_2$ is added under argon to a solution of 3.0 g (13.9 mmol) of methyl 2-bromonicotinate in 10 ml of dioxane and the mixture is stirred for 30 min at room temperature. Thereafter, 3.33 g (13.78 mmol) of 2-chloro-6-(4,4,5,5-tetramethyl-1,3,2-dioxaborolan-2-yl)pyridine, 5.76 g (41.68 mmol) of $K_2CO_3$ and 11 ml of $H_2O$ are added in succession to the mixture, and the mixture is stirred for 6 hours under reflux and subsequently allowed to stand overnight at room temperature (RT). For work-up, the reaction mixture is poured into 150 ml of $H_2O$ and extracted repeatedly with $CH_2Cl_2$. The combined organic phases are dried over $Na_2SO_4$ and subsequently concentrated. The crude product thus obtained is purified by chromatography on silica gel using heptane/ethyl acetate (7:3) as the mobile phase. This gives 2.50 g (72%) of product as a colorless oil; $^1H$ NMR (CDCl$_3$) δ 8.70 (dd, 1H), 8.15 (dd, 1H), 7.95 (dd, 1H), 7.80 (dd, 1H), 7.40 (dd, 1H), 7.37 (dd, 1H), 3.90 (s, 3H, COOMe).

2. Methyl 6'-(4-chlorophenyl)-2,2'-bipyridine-3-carboxylate (2)

0.21 g (0.30 mmol) of (Ph$_3$P)$_2$PdCl$_2$ is added under argon to a solution of 2.5 g (10.05 mmol) of methyl 6'-chloro-2,2'-bipyridine-3-carboxylate (1) in 70 ml of dioxane and the mixture is stirred for 30 min at room temperature. Thereafter, 1.98 g (12.08 mmol) of para-chlorophenylboronic acid, 4.17 g (30.17 mmol) of K$_2$CO$_3$ and 7 ml of H$_2$O are added in succession to the mixture, and the mixture is stirred for 6 hours under reflux and subsequently left to stand overnight at RT. For work-up, the reaction mixture is poured into 100 ml of H$_2$O and extracted repeatedly with CH$_2$Cl$_2$. The combined organic phases are dried over Na$_2$SO$_4$ and concentrated. The residue is purified by column chromatography over silica gel using heptane/ethyl acetate (7:3) as the mobile phase. This gives 2.7 g (82.7%) of product as a solid. M.p.: 120.5° C.; $^1$H NMR (CDCl$_3$) δ 8.75 (dd, 1H), 8.17 (dd, 1H), 8.00 (m, 2H, C$_6$H$_4$Cl), 7.95 (dd, 1H), 7.92 (dd, 1H), 7.28 (dd, 1H), 7.45 (m, 2H, C$_6$H$_4$Cl), 7.40 (dd, 1H), 3.60 (s, 3H, COOMe).

3. 6'-(4-Chlorophenyl)-2,2'-bipyridine-3-carboxylic acid (3)

A solution of 0.23 g (0.71 mmol) of methyl 6'-(4-chlorophenyl)-2,2'-bipyridine-3-carboxylate (2) and 0.04 g (0.99 mmol) of NaOH in 6 ml of THF and 2.5 ml of H$_2$O is stirred for 4 hours at 50° C. and subsequently left to stand at RT for 12 hours. For work-up, THF is removed by rotary evaporation, and the aqueous residue is extracted with a little CH$_2$Cl$_2$. The aqueous phase is brought to pH 2 using 1 N HCl, whereupon a viscose crystal slurry is obtained as the product. This gives 70 mg (32%) of product as a solid; m.p.: 221° C.; $^1$H NMR (CDCl$_3$) δ 8.85 (dd, 1H), 8.79 (dd, 1H), 8.62 (dd, 1H), 8.15 (dd, 1H), 7.85 (m, 2H, C$_6$H$_4$Cl), 7.82 (dd, 1H), 7.54 (m, 2H, C$_6$H$_4$Cl), 7.51 (d, 1H).

4. Potassium 6'-(4-chlorophenyl)-2,2'-bipyridine-3-carboxylic acid (4)

0.008 g of KOH, dissolved in 10 ml of MeOH/H$_2$O (1/1), is added to a solution of 0.042 g (0.13 mmol) of 6'-(4-chlorophenyl)-2,2'-bipyridine-3-carboxylic acid (3) in 8 ml of a solvent mixture of dioxane/methanol (8/2), and this mixture is stirred for 1 hour at 40° C. Thereafter, the solution is evaporated to dryness. This gives 40 mg (93%) of product as an amorphous solid. $^1$H NMR (DMSO) δ 8.41 (dd, 1H), 8.30 (m, 2H, C$_6$H$_4$Cl), 7.90 (m, 2H), 7.75 (d, 2H), 7.70 (d, 2H), 7.50 (m, 2H, C$_6$H$_4$Cl), 7.25 (dd, 1H).

The examples listed in the tables below were prepared analogously to the abovementioned methods or are obtainable analogously to the abovementioned methods. The compounds listed therein are very especially preferred. The abbreviation Me stands for methyl. If the symbols K or Na are given for the radical R$^2$, this means that the respective compound according to the invention is present in the form of its sodium or potassium salt.

TABLE 1

Inventive compounds of the formula (I), wherein R$^1$, R$^3$ and R$^4$ are each hydrogen, and R$^2$ and R$^5$ have the meanings given in Table 1

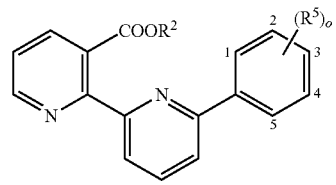

| Ex. No. | R$^2$ | R$^5$ |
|---|---|---|
| 1.001 | Me | — |
| 1.002 | Me | 3-Cl |
| 1.003 | Me | 3,4-Cl$_2$ |
| 1.004 | Me | 3,4,5-Cl$_3$ |
| 1.005 | Me | 3,5-Cl$_2$ |
| 1.006 | Me | 3,5-Cl$_2$-4-OMe |
| 1.007 | Me | 3,5-Cl$_2$-4-F |
| 1.008 | Me | 2,4-Cl$_2$ |
| 1.009 | Me | 2,3,4-Cl$_3$ |
| 1.010 | Me | 2,4-Cl$_2$-3-F |
| 1.011 | Me | 2,4-Cl$_2$-3-OMe |
| 1.012 | Me | 2,4-Cl$_2$-3-Me |
| 1.013 | Me | 2,4,5-Cl$_3$ |
| 1.014 | Me | 2-Cl-4-F |
| 1.015 | Me | 2-Cl-4-OMe |
| 1.016 | Me | 2-Cl-4-Me |
| 1.017 | Me | 3-F |
| 1.018 | Me | 4-Cl-3-F |
| 1.019 | Me | 3,4-F$_2$ |
| 1.020 | Me | 3,4,5-F$_3$ |
| 1.021 | Me | 3,5-F$_2$-4-Me |
| 1.022 | Me | 3,5-F$_2$-4-OMe |
| 1.023 | Me | 2,4-F$_2$ |
| 1.024 | Me | 3-Cl-4-F |
| 1.025 | Me | 2,4-F$_2$-3-OMe |
| 1.026 | Me | 2-F-4-OMe |
| 1.027 | Me | 4-Cl-2-F |
| 1.028 | Me | 2,3,5-F$_3$ |
| 1.029 | Me | 5-Cl-2,3-F$_2$ |
| 1.030 | Me | 2-F-4-Me |
| 1.031 | Me | 5-Cl-3-F-4-OMe |
| 1.032 | Me | 3,5-F$_2$-4-NMe$_2$ |
| 1.033 | Me | 5-Cl-3-F-4-NMe$_2$ |
| 1.034 | Me | 2-F-4-NMe$_2$ |
| 1.035 | Me | 2-F-4-NH$_2$ |
| 1.036 | Me | 3,4-Cl$_2$-2-F |
| 1.037 | Me | 3,4,5-Cl$_3$-2-F |
| 1.038 | Me | 2,5-F$_2$-4-OMe |
| 1.039 | Me | 5-Cl-2-F-4-OMe |
| 1.040 | Me | 3-CF$_3$ |
| 1.041 | Me | 2-Cl-3-CF$_3$ |
| 1.042 | Me | 2,4-Cl$_2$-3-CF$_3$ |
| 1.043 | Me | 4-Cl-3-CF$_3$ |
| 1.044 | Me | 5-Cl-3-CF$_3$ |
| 1.045 | Me | 3-CF$_3$-2-F |
| 1.046 | Me | 3-CF$_3$-2,4-F$_2$ |
| 1.047 | Me | 3-CF$_3$-4-F |
| 1.048 | Me | 3-CF$_3$-5-F |
| 1.049 | Me | 4-CF$_3$ |
| 1.050 | Me | 3-Cl-4-CF$_3$ |
| 1.051 | Me | 3,5-Cl$_2$-4CF$_3$ |
| 1.052 | Me | 5-Cl-4-CF$_3$ |
| 1.053 | Me | 4-SMe |
| 1.054 | Me | 3-Cl-4-SMe |
| 1.055 | Me | 5-Cl-4-SMe |
| 1.056 | Me | 3,5-Cl$_2$-4-SMe |
| 1.057 | Me | 3-F-4-SMe |
| 1.058 | Me | 3,5-F$_2$-4-SMe |
| 1.059 | Me | 5-F-4-SMe |
| 1.060 | Me | 3-Cl-5-F-4-SMe |
| 1.061 | H | — |
| 1.062 | H | 3-Cl |
| 1.063 | H | 3,4-Cl$_2$ |
| 1.064 | H | 3,4,5-Cl$_3$ |
| 1.065 | H | 3,5-Cl$_2$ |

TABLE 1-continued

Inventive compounds of the formula (I), wherein $R^1$, $R^3$ and $R^4$ are each hydrogen, and $R^2$ and $R^5$ have the meanings given in Table 1

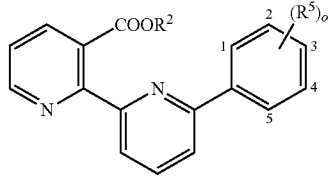

| Ex. No. | $R^2$ | $R^5$ |
|---|---|---|
| 1.066 | H | 3,5-Cl$_2$-4-OMe |
| 1.067 | H | 3,5-Cl$_2$-4-F |
| 1.068 | H | 2,4-Cl$_2$ |
| 1.069 | H | 2,3,4-Cl$_3$ |
| 1.070 | H | 2,4-Cl$_2$-3-F |
| 1.071 | H | 2,4-Cl$_2$-3-OMe |
| 1.072 | H | 2,4-Cl$_2$-3-Me |
| 1.073 | H | 2,4,5-Cl$_3$ |
| 1.074 | H | 2-Cl-4-F |
| 1.075 | H | 2-Cl-4-OMe |
| 1.076 | H | 2-Cl-4-Me |
| 1.077 | H | 3-F |
| 1.078 | H | 4-Cl-3-F |
| 1.079 | H | 3,4-F$_2$ |
| 1.080 | H | 3,4,5-F$_3$ |
| 1.081 | H | 3,5-F$_2$-4-Me |
| 1.082 | H | 3,5-F$_2$-4-OMe |
| 1.083 | H | 2,4-F$_2$ |
| 1.084 | H | 3-Cl-4-F |
| 1.085 | H | 2,4-F$_2$-3-OMe |
| 1.086 | H | 2-F-4-OMe |
| 1.087 | H | 4-Cl-2-F |
| 1.088 | H | 2,3,5-F$_3$ |
| 1.089 | H | 5-Cl-2,3-F$_2$ |
| 1.090 | H | 2-F-4-Me |
| 1.091 | H | 5-Cl-3-F-4-OMe |
| 1.092 | H | 3,5-F$_2$-4-NMe$_2$ |
| 1.093 | H | 5-Cl-3-F-4-NMe$_2$ |
| 1.094 | H | 2-F-4-NMe$_2$ |
| 1.095 | H | 2-F-4-NH$_2$ |
| 1.096 | H | 3,4-Cl$_2$-2-F |
| 1.097 | H | 3,4,5-Cl$_3$-2-F |
| 1.098 | H | 2,5-F$_2$-4-OMe |
| 1.099 | H | 5-Cl-2-F-4-OMe |
| 1.100 | H | 3-CF$_3$ |
| 1.101 | H | 2-Cl-3-CF$_3$ |
| 1.102 | H | 2,4-Cl$_2$-3-CF$_3$ |
| 1.103 | H | 4-Cl-3-CF$_3$ |
| 1.104 | H | 5-Cl-3-CF$_3$ |
| 1.105 | H | 3-CF$_3$-2-F |
| 1.106 | H | 3-CF$_3$-2,4-F$_2$ |
| 1.107 | H | 3-CF$_3$-4-F |
| 1.108 | H | 3-CF$_3$-5-F |
| 1.109 | H | 4-CF$_3$ |
| 1.110 | H | 3-Cl-4-CF$_3$ |
| 1.111 | H | 3,5-Cl$_2$-4CF$_3$ |
| 1.112 | H | 5-Cl-4-CF$_3$ |
| 1.113 | H | 4-SMe |
| 1.114 | H | 3-Cl-4-SMe |
| 1.115 | H | 5-Cl-4-SMe |
| 1.116 | H | 3,5-Cl$_2$-4-SMe |
| 1.117 | H | 3-F-4-SMe |
| 1.118 | H | 3,5-F$_2$-4-SMe |
| 1.119 | H | 5-F-4-SMe |
| 1.120 | H | 3-Cl-5-F-4-SMe |
| 1.121 | Na | — |
| 1.122 | Na | 3-Cl |
| 1.123 | Na | 3,4-Cl$_2$ |
| 1.124 | Na | 3,4,5-Cl$_3$ |
| 1.125 | Na | 3,5-Cl$_2$ |
| 1.126 | Na | 3,5-Cl$_2$-4-OMe |
| 1.127 | Na | 3,5-Cl$_2$-4-F |
| 1.128 | Na | 2,4-Cl$_2$ |
| 1.129 | Na | 2,3,4-Cl$_3$ |
| 1.130 | Na | 2,4-Cl$_2$-3-F |

TABLE 1-continued

Inventive compounds of the formula (I), wherein $R^1$, $R^3$ and $R^4$ are each hydrogen, and $R^2$ and $R^5$ have the meanings given in Table 1

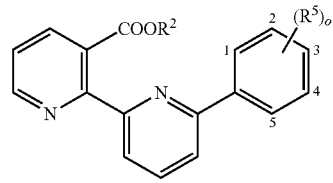

| Ex. No. | $R^2$ | $R^5$ |
|---|---|---|
| 1.131 | Na | 2,4-Cl$_2$-3-OMe |
| 1.132 | Na | 2,4-Cl$_2$-3-Me |
| 1.133 | Na | 2,4,5-Cl$_3$ |
| 1.134 | Na | 2-Cl-4-F |
| 1.135 | Na | 2-Cl-4-OMe |
| 1.136 | Na | 2-Cl-4-Me |
| 1.137 | Na | 3-F |
| 1.138 | Na | 4-Cl-3-F |
| 1.139 | Na | 3,4-F$_2$ |
| 1.140 | Na | 3,4,5-F$_3$ |
| 1.141 | Na | 3,5-F$_2$-4-Me |
| 1.142 | Na | 3,5-F$_2$-4-OMe |
| 1.143 | Na | 2,4-F$_2$ |
| 1.144 | Na | 3-Cl-4-F |
| 1.145 | Na | 2,4-F$_2$-3-OMe |
| 1.146 | Na | 2-F-4-OMe |
| 1.147 | Na | 4-Cl-2-F |
| 1.148 | Na | 2,3,5-F$_3$ |
| 1.149 | Na | 5-Cl-2,3-F$_2$ |
| 1.150 | Na | 2-F-4-Me |
| 1.151 | Na | 5-Cl-3-F-4-OMe |
| 1.152 | Na | 3,5-F$_2$-4-NMe$_2$ |
| 1.153 | Na | 5-Cl-3-F-4-NMe$_2$ |
| 1.154 | Na | 2-F-4-NMe$_2$ |
| 1.155 | Na | 2-F-4-NH$_2$ |
| 1.156 | Na | 3,4-Cl$_2$-2-F |
| 1.157 | Na | 3,4,5-Cl$_3$-2-F |
| 1.158 | Na | 2,5-F$_2$-4-OMe |
| 1.159 | Na | 5-Cl-2-F-4-OMe |
| 1.160 | Na | 3-CF$_3$ |
| 1.161 | Na | 2-Cl-3-CF$_3$ |
| 1.162 | Na | 2,4-Cl$_2$-3-CF$_3$ |
| 1.163 | Na | 4-Cl-3-CF$_3$ |
| 1.164 | Na | 5-Cl-3-CF$_3$ |
| 1.165 | Na | 3-CF$_3$-2-F |
| 1.166 | Na | 3-CF$_3$-2,4-F$_2$ |
| 1.167 | Na | 3-CF$_3$-4-F |
| 1.168 | Na | 3-CF$_3$-5-F |
| 1.169 | Na | 4-CF$_3$ |
| 1.170 | Na | 3-Cl-4-CF$_3$ |
| 1.171 | Na | 3,5-Cl$_2$-4CF$_3$ |
| 1.172 | Na | 5-Cl-4-CF$_3$ |
| 1.173 | Na | 4-SMe |
| 1.174 | Na | 3-Cl-4-SMe |
| 1.175 | Na | 5-Cl-4-SMe |
| 1.176 | Na | 3,5-Cl$_2$-4-SMe |
| 1.177 | Na | 3-F-4-SMe |
| 1.178 | Na | 3,5-F$_2$-4-SMe |
| 1.179 | Na | 5-F-4-SMe |
| 1.180 | Na | 3-Cl-5-F-4-SMe |
| 1.181 | K | — |
| 1.182 | K | 3-Cl |
| 1.183 | K | 3,4-Cl$_2$ |
| 1.184 | K | 3,4,5-Cl$_3$ |
| 1.185 | K | 3,5-Cl$_2$ |
| 1.186 | K | 3,5-Cl$_2$-4-OMe |
| 1.187 | K | 3,5-Cl$_2$-4-F |
| 1.188 | K | 2,4-Cl$_2$ |
| 1.189 | K | 2,3,4-Cl$_3$ |
| 1.190 | K | 2,4-Cl$_2$-3-F |
| 1.191 | K | 2,4-Cl$_2$-3-OMe |
| 1.192 | K | 2,4-Cl$_2$-3-Me |
| 1.193 | K | 2,4,5-Cl$_3$ |
| 1.194 | K | 2-Cl-4-F |
| 1.195 | K | 2-Cl-4-OMe |

TABLE 1-continued

Inventive compounds of the formula (I), wherein $R^1$, $R^3$ and $R^4$ are each hydrogen, and $R^2$ and $R^5$ have the meanings given in Table 1

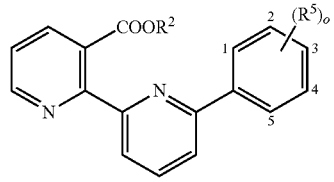

| Ex. No. | $R^2$ | $R^5$ |
|---|---|---|
| 1.196 | K | 2-Cl-4-Me |
| 1.197 | K | 3-F |
| 1.198 | K | 4-Cl-3-F |
| 1.199 | K | 3,4-F$_2$ |
| 1.200 | K | 3,4,5-F$_3$ |
| 1.201 | K | 3,5-F$_2$-4-Me |
| 1.202 | K | 3,5-F$_2$-4-OMe |
| 1.203 | K | 2,4-F$_2$ |
| 1.204 | K | 3-Cl-4-F |
| 1.205 | K | 2,4-F$_2$-3-OMe |
| 1.206 | K | 2-F-4-OMe |
| 1.207 | K | 4-Cl-2-F |
| 1.208 | K | 2,3,5-F$_3$ |
| 1.209 | K | 5-Cl-2,3-F$_2$ |
| 1.210 | K | 2-F-4-Me |
| 1.211 | K | 5-Cl-3-F-4-OMe |
| 1.212 | K | 3,5-F$_2$-4-NMe$_2$ |
| 1.213 | K | 5-Cl-3-F-4-NMe$_2$ |
| 1.214 | K | 2-F-4-NMe$_2$ |
| 1.215 | K | 2-F-4-NH$_2$ |
| 1.216 | K | 3,4-Cl$_2$-2-F |
| 1.217 | K | 3,4,5-Cl$_3$-2-F |
| 1.218 | K | 2,5-F$_2$-4-OMe |
| 1.219 | K | 5-Cl-2-F-4-OMe |
| 1.220 | K | 3-CF$_3$ |
| 1.221 | K | 2-Cl-3-CF$_3$ |
| 1.222 | K | 2,4-Cl$_2$-3-CF$_3$ |
| 1.223 | K | 4-Cl-3-CF$_3$ |
| 1.224 | K | 5-Cl-3-CF$_3$ |
| 1.225 | K | 3-CF$_3$-2-F |
| 1.226 | K | 3-CF$_3$-2,4-F$_2$ |
| 1.227 | K | 3-CF$_3$-4-F |
| 1.228 | K | 3-CF$_3$-5-F |
| 1.229 | K | 4-CF$_3$ |
| 1.230 | K | 3-Cl-4-CF$_3$ |
| 1.231 | K | 3,5-Cl$_2$-4CF$_3$ |
| 1.232 | K | 5-Cl-4-CF$_3$ |
| 1.233 | K | 4-SMe |
| 1.234 | K | 3-Cl-4-SMe |
| 1.235 | K | 5-Cl-4-SMe |
| 1.236 | K | 3,5-Cl$_2$-4-Sme |
| 1.237 | K | 3-F-4-SMe |
| 1.238 | K | 3,5-F$_2$-4-SMe |
| 1.239 | K | 5-F-4-SMe |
| 1.240 | K | 3-Cl-5-F-4-SMe |
| 1.241 | Me | 3-Cl-5-F |
| 1.242 | K | 3-Cl-5-F |

TABLE 2

Inventive compounds of the formula (I), wherein $R^1$ and $R^4$ are each hydrogen, $R^3$ is chlorine and $R^2$ and $R^5$ have the meanings given in Table 1.

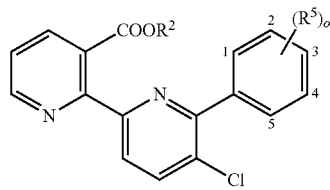

| Ex. No. | $R^2$ | $R^5$ |
|---|---|---|
| 2.001 | Me | — |
| 2.002 | Me | 3-Cl |
| 2.003 | Me | 3,4-Cl$_2$ |
| 2.004 | Me | 3,4,5-Cl$_3$ |
| 2.005 | Me | 3,5-Cl$_2$ |
| 2.006 | Me | 3,5-Cl$_2$-4-OMe |
| 2.007 | Me | 3,5-Cl$_2$-4-F |
| 2.008 | Me | 2,4-Cl$_2$ |
| 2.009 | Me | 2,3,4-Cl$_3$ |
| 2.010 | Me | 2,4-Cl$_2$-3-F |
| 2.011 | Me | 2,4-Cl$_2$-3-OMe |
| 2.012 | Me | 2,4-Cl$_2$-3-Me |
| 2.013 | Me | 2,4,5-Cl$_3$ |
| 2.014 | Me | 2-Cl-4-F |
| 2.015 | Me | 2-Cl-4-OMe |
| 2.016 | Me | 2-Cl-4-Me |
| 2.017 | Me | 3-F |
| 2.018 | Me | 4-Cl-3-F |
| 2.019 | Me | 3,4-F$_2$ |
| 2.020 | Me | 3,4,5-F$_3$ |
| 2.021 | Me | 3,5-F$_2$-4-Me |
| 2.022 | Me | 3,5-F$_2$-4-OMe |
| 2.023 | Me | 2,4-F$_2$ |
| 2.024 | Me | 3-Cl-4-F |
| 2.025 | Me | 2,4-F$_2$-3-OMe |
| 2.026 | Me | 2-F-4-OMe |
| 2.027 | Me | 4-Cl-2-F |
| 2.028 | Me | 2,3,5-F$_3$ |
| 2.029 | Me | 5-Cl-2,3-F$_2$ |
| 2.030 | Me | 2-F-4-Me |
| 2.031 | Me | 5-Cl-3-F-4-OMe |
| 2.032 | Me | 3,5-F$_2$-4-NMe$_2$ |
| 2.033 | Me | 5-Cl-3-F-4-NMe$_2$ |
| 2.034 | Me | 2-F-4-NMe$_2$ |
| 2.035 | Me | 2-F-4-NH$_2$ |
| 2.036 | Me | 3,4-Cl$_2$-2-F |
| 2.037 | Me | 3,4,5-Cl$_3$-2-F |
| 2.038 | Me | 2,5-F$_2$-4-OMe |
| 2.039 | Me | 5-Cl-2-F-4-OMe |
| 2.040 | Me | 3-CF$_3$ |
| 2.041 | Me | 2-Cl-3-CF$_3$ |
| 2.042 | Me | 2,4-Cl$_2$-3-CF$_3$ |
| 2.043 | Me | 4-Cl-3-CF$_3$ |
| 2.044 | Me | 5-Cl-3-CF$_3$ |
| 2.045 | Me | 3-CF$_3$-2-F |
| 2.046 | Me | 3-CF$_3$-2,4-F$_2$ |
| 2.047 | Me | 3-CF$_3$-4-F |
| 2.048 | Me | 3-CF$_3$-5-F |
| 2.049 | Me | 4-CF$_3$ |
| 2.050 | Me | 3-Cl-4-CF$_3$ |
| 2.051 | Me | 3,5-Cl$_2$-4CF$_3$ |
| 2.052 | Me | 5-Cl-4-CF$_3$ |
| 2.053 | Me | 4-SMe |
| 2.054 | Me | 3-Cl-4-SMe |
| 2.055 | Me | 5-Cl-4-SMe |
| 2.056 | Me | 3,5-Cl$_2$-4-SMe |
| 2.057 | Me | 3-F-4-SMe |
| 2.058 | Me | 3,5-F$_2$-4-SMe |
| 2.059 | Me | 5-F-4-SMe |
| 2.060 | Me | 3-Cl-5-F-4-SMe |
| 2.061 | H | — |
| 2.062 | H | 3-Cl |
| 2.063 | H | 3,4-Cl$_2$ |
| 2.064 | H | 3,4,5-Cl$_3$ |
| 2.065 | H | 3,5-Cl$_2$ |

TABLE 2-continued

Inventive compounds of the formula (I), wherein $R^1$ and $R^4$ are each hydrogen, $R^3$ is chlorine and $R^2$ and $R^5$ have the meanings given in Table 1.

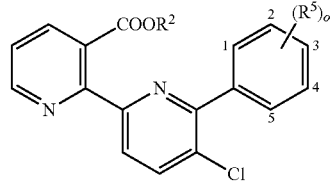

| Ex. No. | $R^2$ | $R^5$ |
|---|---|---|
| 2.066 | H | 3,5-Cl$_2$-4-OMe |
| 2.067 | H | 3,5-Cl$_2$-4-F |
| 2.068 | H | 2,4-Cl$_2$ |
| 2.069 | H | 2,3,4-Cl$_3$ |
| 2.070 | H | 2,4-Cl$_2$-3-F |
| 2.071 | H | 2,4-Cl$_2$-3-OMe |
| 2.072 | H | 2,4-Cl$_2$-3-Me |
| 2.073 | H | 2,4,5-Cl$_3$ |
| 2.074 | H | 2-Cl-4-F |
| 2.075 | H | 2-Cl-4-OMe |
| 2.076 | H | 2-Cl-4-Me |
| 2.077 | H | 3-F |
| 2.078 | H | 4-Cl-3-F |
| 2.079 | H | 3,4-F$_2$ |
| 2.080 | H | 3,4,5-F$_3$ |
| 2.081 | H | 3,5-F$_2$-4-Me |
| 2.082 | H | 3,5-F$_2$-4-OMe |
| 2.083 | H | 2,4-F$_2$ |
| 2.084 | H | 3-Cl-4-F |
| 2.085 | H | 2,4-F$_2$-3-OMe |
| 2.086 | H | 2-F-4-OMe |
| 2.087 | H | 4-Cl-2-F |
| 2.088 | H | 2,3,5-F$_3$ |
| 2.089 | H | 5-Cl-2,3-F$_2$ |
| 2.090 | H | 2-F-4-Me |
| 2.091 | H | 5-Cl-3-F-4-OMe |
| 2.092 | H | 3,5-F$_2$-4-NMe$_2$ |
| 2.093 | H | 5-Cl-3-F-4-NMe$_2$ |
| 2.094 | H | 2-F-4-NMe$_2$ |
| 2.095 | H | 2-F-4-NH$_2$ |
| 2.096 | H | 3,4-Cl$_2$-2-F |
| 2.097 | H | 3,4,5-Cl$_3$-2-F |
| 2.098 | H | 2,5-F$_2$-4-OMe |
| 2.099 | H | 5-Cl-2-F-4-OMe |
| 2.100 | H | 3-CF$_3$ |
| 2.101 | H | 2-Cl-3-CF$_3$ |
| 2.102 | H | 2,4-Cl$_2$-3-CF$_3$ |
| 2.103 | H | 4-Cl-3-CF$_3$ |
| 2.104 | H | 5-Cl-3-CF$_3$ |
| 2.105 | H | 3-CF$_3$-2-F |
| 2.106 | H | 3-CF$_3$-2,4-F$_2$ |
| 2.107 | H | 3-CF$_3$-4-F |
| 2.108 | H | 3-CF$_3$-5-F |
| 2.109 | H | 4-CF$_3$ |
| 2.110 | H | 3-Cl-4-CF$_3$ |
| 2.111 | H | 3,5-Cl$_2$-4CF$_3$ |
| 2.112 | H | 5-Cl-4-CF$_3$ |
| 2.113 | H | 4-SMe |
| 2.114 | H | 3-Cl-4-SMe |
| 2.115 | H | 5-Cl-4-SMe |
| 2.116 | H | 3,5-Cl$_2$-4-SMe |
| 2.117 | H | 3-F-4-SMe |
| 2.118 | H | 3,5-F$_2$-4-SMe |
| 2.119 | H | 5-F-4-SMe |
| 2.120 | H | 3-Cl-5-F-4-SMe |
| 2.121 | Na | — |
| 2.122 | Na | 3-Cl |
| 2.123 | Na | 3,4-Cl$_2$ |
| 2.124 | Na | 3,4,5-Cl$_3$ |
| 2.125 | Na | 3,5-Cl$_2$ |
| 2.126 | Na | 3,5-Cl$_2$-4-OMe |
| 2.127 | Na | 3,5-Cl$_2$-4-F |
| 2.128 | Na | 2,4-Cl$_2$ |
| 2.129 | Na | 2,3,4-Cl$_3$ |
| 2.130 | Na | 2,4-Cl$_2$-3-F |
| 2.131 | Na | 2,4-Cl$_2$-3-OMe |
| 2.132 | Na | 2,4-Cl$_2$-3-Me |
| 2.133 | Na | 2,4,5-Cl$_3$ |
| 2.134 | Na | 2-Cl-4-F |
| 2.135 | Na | 2-Cl-4-OMe |
| 2.136 | Na | 2-Cl-4-Me |
| 2.137 | Na | 3-F |
| 2.138 | Na | 4-Cl-3-F |
| 2.139 | Na | 3,4-F$_2$ |
| 2.140 | Na | 3,4,5-F$_3$ |
| 2.141 | Na | 3,5-F$_2$-4-Me |
| 2.142 | Na | 3,5-F$_2$-4-OMe |
| 2.143 | Na | 2,4-F$_2$ |
| 2.144 | Na | 3-Cl-4-F |
| 2.145 | Na | 2,4-F$_2$-3-OMe |
| 2.146 | Na | 2-F-4-OMe |
| 2.147 | Na | 4-Cl-2-F |
| 2.148 | Na | 2,3,5-F$_3$ |
| 2.149 | Na | 5-Cl-2,3-F$_2$ |
| 2.150 | Na | 2-F-4-Me |
| 2.151 | Na | 5-Cl-3-F-4-OMe |
| 2.152 | Na | 3,5-F$_2$-4-NMe$_2$ |
| 2.153 | Na | 5-Cl-3-F-4-NMe$_2$ |
| 2.154 | Na | 2-F-4-NMe$_2$ |
| 2.155 | Na | 2-F-4-NH$_2$ |
| 2.156 | Na | 3,4-Cl$_2$-2-F |
| 2.157 | Na | 3,4,5-Cl$_3$-2-F |
| 2.158 | Na | 2,5-F$_2$-4-OMe |
| 2.159 | Na | 5-Cl-2-F-4-OMe |
| 2.160 | Na | 3-CF$_3$ |
| 2.161 | Na | 2-Cl-3-CF$_3$ |
| 2.162 | Na | 2,4-Cl$_2$-3-CF$_3$ |
| 2.163 | Na | 4-Cl-3-CF$_3$ |
| 2.164 | Na | 5-Cl-3-CF$_3$ |
| 2.165 | Na | 3-CF$_3$-2-F |
| 2.166 | Na | 3-CF$_3$-2,4-F$_2$ |
| 2.167 | Na | 3-CF$_3$-4-F |
| 2.168 | Na | 3-CF$_3$-5-F |
| 2.169 | Na | 4-CF$_3$ |
| 2.170 | Na | 3-Cl-4-CF$_3$ |
| 2.171 | Na | 3,5-Cl$_2$-4CF$_3$ |
| 2.172 | Na | 5-Cl-4-CF$_3$ |
| 2.173 | Na | 4-SMe |
| 2.174 | Na | 3-Cl-4-SMe |
| 2.175 | Na | 5-Cl-4-SMe |
| 2.176 | Na | 3,5-Cl$_2$-4-SMe |
| 2.177 | Na | 3-F-4-SMe |
| 2.178 | Na | 3,5-F$_2$-4-SMe |
| 2.179 | Na | 5-F-4-SMe |
| 2.180 | Na | 3-Cl-5-F-4-SMe |
| 2.181 | K | — |
| 2.182 | K | 3-Cl |
| 2.183 | K | 3,4-Cl$_2$ |
| 2.184 | K | 3,4,5-Cl$_3$ |
| 2.185 | K | 3,5-Cl$_2$ |
| 2.186 | K | 3,5-Cl$_2$-4-OMe |
| 2.187 | K | 3,5-Cl$_2$-4-F |
| 2.188 | K | 2,4-Cl$_2$ |
| 2.189 | K | 2,3,4-Cl$_3$ |
| 2.190 | K | 2,4-Cl$_2$-3-F |
| 2.191 | K | 2,4-Cl$_2$-3-OMe |
| 2.192 | K | 2,4-Cl$_2$-3-Me |
| 2.193 | K | 2,4,5-Cl$_3$ |
| 2.194 | K | 2-Cl-4-F |
| 2.195 | K | 2-Cl-4-OMe |

TABLE 2-continued

Inventive compounds of the formula (I), wherein $R^1$ and $R^4$ are each hydrogen, $R^3$ is chlorine and $R^2$ and $R^5$ have the meanings given in Table 1.

| Ex. No. | $R^2$ | $R^5$ |
|---|---|---|
| 2.196 | K | 2-Cl-4-Me |
| 2.197 | K | 3-F |
| 2.198 | K | 4-Cl-3-F |
| 2.199 | K | 3,4-F$_2$ |
| 2.200 | K | 3,4,5-F$_3$ |
| 2.201 | K | 3,5-F$_2$-4-Me |
| 2.202 | K | 3,5-F$_2$-4-OMe |
| 2.203 | K | 2,4-F$_2$ |
| 2.204 | K | 3-Cl-4-F |
| 2.205 | K | 2,4-F$_2$-3-OMe |
| 2.206 | K | 2-F-4-OMe |
| 2.207 | K | 4-Cl-2-F |
| 2.208 | K | 2,3,5-F$_3$ |
| 2.209 | K | 5-Cl-2,3-F$_2$ |
| 2.210 | K | 2-F-4-Me |
| 2.211 | K | 5-Cl-3-F-4-OMe |
| 2.212 | K | 3,5-F$_2$-4-NMe$_2$ |
| 2.213 | K | 5-Cl-3-F-4-NMe$_2$ |
| 2.214 | K | 2-F-4-NMe$_2$ |
| 2.215 | K | 2-F-4-NH$_2$ |
| 2.216 | K | 3,4-Cl$_2$-2-F |
| 2.217 | K | 3,4,5-Cl$_3$-2-F |
| 2.218 | K | 2,5-F$_2$-4-OMe |
| 2.219 | K | 5-Cl-2-F-4-OMe |
| 2.220 | K | 3-CF$_3$ |
| 2.221 | K | 2-Cl-3-CF$_3$ |
| 2.222 | K | 2,4-Cl$_2$-3-CF$_3$ |
| 2.223 | K | 4-Cl-3-CF$_3$ |
| 2.224 | K | 5-Cl-3-CF$_3$ |
| 2.225 | K | 3-CF$_3$-2-F |
| 2.226 | K | 3-CF$_3$-2,4-F$_2$ |
| 2.227 | K | 3-CF$_3$-4-F |
| 2.228 | K | 3-CF$_3$-5-F |
| 2.229 | K | 4-CF$_3$ |
| 2.230 | K | 3-Cl-4-CF$_3$ |
| 2.231 | K | 3,5-Cl$_2$-4CF$_3$ |
| 2.232 | K | 5-Cl-4-CF$_3$ |
| 2.233 | K | 4-SMe |
| 2.234 | K | 3-Cl-4-SMe |
| 2.235 | K | 5-Cl-4-SMe |
| 2.236 | K | 3,5-Cl$_2$-4-SMe |
| 2.237 | K | 3-F-4-SMe |
| 2.238 | K | 3,5-F$_2$-4-SMe |
| 2.239 | K | 5-F-4-SMe |
| 2.240 | K | 3-Cl-5-F-4-SMe |

TABLE 3

Inventive compounds of the formula (I) wherein $R^1$ and $R^4$ are each hydrogen, $R^3$ is fluorine, and $R^2$ and $R^5$ ave the meanings given in Table 1

| Ex. No. | $R^2$ | $R^5$ |
|---|---|---|
| 3.001 | Me | — |
| 3.002 | Me | 3-Cl |
| 3.003 | Me | 3,4-Cl$_2$ |
| 3.004 | Me | 3,4,5-Cl$_3$ |
| 3.005 | Me | 3,5-Cl$_2$ |
| 3.006 | Me | 3,5-Cl$_2$-4-OMe |
| 3.007 | Me | 3,5-Cl$_2$-4-F |
| 3.008 | Me | 2,4-Cl$_2$ |
| 3.009 | Me | 2,3,4-Cl$_3$ |
| 3.010 | Me | 2,4-Cl$_2$-3-F |
| 3.011 | Me | 2,4-Cl$_2$-3-OMe |
| 3.012 | Me | 2,4-Cl$_2$-3-Me |
| 3.013 | Me | 2,4,5-Cl$_3$ |
| 3.014 | Me | 2-Cl-4-F |
| 3.015 | Me | 2-Cl-4-OMe |
| 3.016 | Me | 2-Cl-4-Me |
| 3.017 | Me | 3-F |
| 3.018 | Me | 4-Cl-3-F |
| 3.019 | Me | 3,4-F$_2$ |
| 3.020 | Me | 3,4,5-F$_3$ |
| 3.021 | Me | 3,5-F$_2$-4-Me |
| 3.022 | Me | 3,5-F$_2$-4-OMe |
| 3.023 | Me | 2,4-F$_2$ |
| 3.024 | Me | 3-Cl-4-F |
| 3.025 | Me | 2,4-F$_2$-3-OMe |
| 3.026 | Me | 2-F-4-OMe |
| 3.027 | Me | 4-Cl-2-F |
| 3.028 | Me | 2,3,5-F$_3$ |
| 3.029 | Me | 5-Cl-2,3-F$_2$ |
| 3.030 | Me | 2-F-4-Me |
| 3.031 | Me | 5-Cl-3-F-4-OMe |
| 3.032 | Me | 3,5-F$_2$-4-NMe$_2$ |
| 3.033 | Me | 5-Cl-3-F-4-NMe$_2$ |
| 3.034 | Me | 2-F-4-NMe$_2$ |
| 3.035 | Me | 2-F-4-NH$_2$ |
| 3.036 | Me | 3,4-Cl$_2$-2-F |
| 3.037 | Me | 3,4,5-Cl$_3$-2-F |
| 3.038 | Me | 2,5-F$_2$-4-OMe |
| 3.039 | Me | 5-Cl-2-F-4-OMe |
| 3.040 | Me | 3-CF$_3$ |
| 3.041 | Me | 2-Cl-3-CF$_3$ |
| 3.042 | Me | 2,4-Cl$_2$-3-CF$_3$ |
| 3.043 | Me | 4-Cl-3-CF$_3$ |
| 3.044 | Me | 5-Cl-3-CF$_3$ |
| 3.045 | Me | 3-CF$_3$-2-F |
| 3.046 | Me | 3-CF$_3$-2,4-F$_2$ |
| 3.047 | Me | 3-CF$_3$-4-F |
| 3.048 | Me | 3-CF$_3$-5-F |
| 3.049 | Me | 4-CF$_3$ |
| 3.050 | Me | 3-Cl-4-CF$_3$ |
| 3.051 | Me | 3,5-Cl$_2$-4CF$_3$ |
| 3.052 | Me | 5-Cl-4-CF$_3$ |
| 3.053 | Me | 4-SMe |
| 3.054 | Me | 3-Cl-4-SMe |
| 3.055 | Me | 5-Cl-4-SMe |
| 3.056 | Me | 3,5-Cl$_2$-4-SMe |
| 3.057 | Me | 3-F-4-SMe |
| 3.058 | Me | 3,5-F$_2$-4-SMe |
| 3.059 | Me | 5-F-4-SMe |
| 3.060 | Me | 3-Cl-5-F-4-SMe |
| 3.061 | H | — |
| 3.062 | H | 3-Cl |
| 3.063 | H | 3,4-Cl$_2$ |
| 3.064 | H | 3,4,5-Cl$_3$ |
| 3.065 | H | 3,5-Cl$_2$ |

TABLE 3-continued

Inventive compounds of the formula (I) wherein $R^1$ and $R^4$ are each hydrogen, $R^3$ is fluorine, and $R^2$ and $R^5$ are the meanings given in Table 1

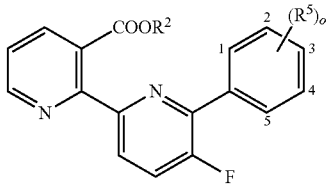

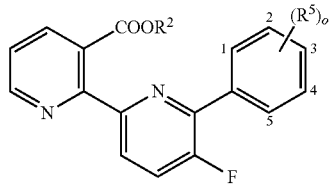

| Ex. No. | $R^2$ | $R^5$ |
|---|---|---|
| 3.066 | H | 3,5-Cl$_2$-4-OMe |
| 3.067 | H | 3,5-Cl$_2$-4-F |
| 3.068 | H | 2,4-Cl$_2$ |
| 3.069 | H | 2,3,4-Cl$_3$ |
| 3.070 | H | 2,4-Cl$_2$-3-F |
| 3.071 | H | 2,4-Cl$_2$-3-OMe |
| 3.072 | H | 2,4-Cl$_2$-3-Me |
| 3.073 | H | 2,4,5-Cl$_3$ |
| 3.074 | H | 2-Cl-4-F |
| 3.075 | H | 2-Cl-4-OMe |
| 3.076 | H | 2-Cl-4-Me |
| 3.077 | H | 3-F |
| 3.078 | H | 4-Cl-3-F |
| 3.079 | H | 3,4-F$_2$ |
| 3.080 | H | 3,4,5-F$_3$ |
| 3.081 | H | 3,5-F$_2$-4-Me |
| 3.082 | H | 3,5-F$_2$-4-OMe |
| 3.083 | H | 2,4-F$_2$ |
| 3.084 | H | 3-Cl-4-F |
| 3.085 | H | 2,4-F$_2$-3-OMe |
| 3.086 | H | 2-F-4-OMe |
| 3.087 | H | 4-Cl-2-F |
| 3.088 | H | 2,3,5-F$_3$ |
| 3.089 | H | 5-Cl-2,3-F$_2$ |
| 3.090 | H | 2-F-4-Me |
| 3.091 | H | 5-Cl-3-F-4-OMe |
| 3.092 | H | 3,5-F$_2$-4-NMe$_2$ |
| 3.093 | H | 5-Cl-3-F-4-NMe$_2$ |
| 3.094 | H | 2-F-4-NMe$_2$ |
| 3.095 | H | 2-F-4-NH$_2$ |
| 3.096 | H | 3,4-Cl$_2$-2-F |
| 3.097 | H | 3,4,5-Cl$_3$-2-F |
| 3.098 | H | 2,5-F$_2$-4-OMe |
| 3.099 | H | 5-Cl-2-F-4-OMe |
| 3.100 | H | 3-CF$_3$ |
| 3.101 | H | 2-Cl-3-CF$_3$ |
| 3.102 | H | 2,4-Cl$_2$-3-CF$_3$ |
| 3.103 | H | 4-Cl-3-CF$_3$ |
| 3.104 | H | 5-Cl-3-CF$_3$ |
| 3.105 | H | 3-CF$_3$-2-F |
| 3.106 | H | 3-CF$_3$-2,4-F$_2$ |
| 3.107 | H | 3-CF$_3$-4-F |
| 3.108 | H | 3-CF$_3$-5-F |
| 3.109 | H | 4-CF$_3$ |
| 3.110 | H | 3-Cl-4-CF$_3$ |
| 3.111 | H | 3,5-Cl$_2$-4CF$_3$ |
| 3.112 | H | 5-Cl-4-CF$_3$ |
| 3.113 | H | 4-SMe |
| 3.114 | H | 3-Cl-4-SMe |
| 3.115 | H | 5-Cl-4-SMe |
| 3.116 | H | 3,5-Cl$_2$-4-SMe |
| 3.117 | H | 3-F-4-SMe |
| 3.118 | H | 3,5-F$_2$-4-SMe |
| 3.119 | H | 5-F-4-SMe |
| 3.120 | H | 3-Cl-5-F-4-SMe |
| 3.121 | Na | — |
| 3.122 | Na | 3-Cl |
| 3.123 | Na | 3,4-Cl$_2$ |
| 3.124 | Na | 3,4,5-Cl$_3$ |
| 3.125 | Na | 3,5-Cl$_2$ |
| 3.126 | Na | 3,5-Cl$_2$-4-OMe |
| 3.127 | Na | 3,5-Cl$_2$-4-F |
| 3.128 | Na | 2,4-Cl$_2$ |
| 3.129 | Na | 2,3,4-Cl$_3$ |
| 3.130 | Na | 2,4-Cl$_2$-3-F |
| 3.131 | Na | 2,4-Cl$_2$-3-OMe |
| 3.132 | Na | 2,4-Cl$_2$-3-Me |
| 3.133 | Na | 2,4,5-Cl$_3$ |
| 3.134 | Na | 2-Cl-4-F |
| 3.135 | Na | 2-Cl-4-OMe |
| 3.136 | Na | 2-Cl-4-Me |
| 3.137 | Na | 3-F |
| 3.138 | Na | 4-Cl-3-F |
| 3.139 | Na | 3,4-F$_2$ |
| 3.140 | Na | 3,4,5-F$_3$ |
| 3.141 | Na | 3,5-F$_2$-4-Me |
| 3.142 | Na | 3,5-F$_2$-4-OMe |
| 3.143 | Na | 2,4-F$_2$ |
| 3.144 | Na | 3-Cl-4-F |
| 3.145 | Na | 2,4-F$_2$-3-OMe |
| 3.146 | Na | 2-F-4-OMe |
| 3.147 | Na | 4-Cl-2-F |
| 3.148 | Na | 2,3,5-F$_3$ |
| 3.149 | Na | 5-Cl-2,3-F$_2$ |
| 3.150 | Na | 2-F-4-Me |
| 3.151 | Na | 5-Cl-3-F-4-OMe |
| 3.152 | Na | 3,5-F$_2$-4-NMe$_2$ |
| 3.153 | Na | 5-Cl-3-F-4-NMe$_2$ |
| 3.154 | Na | 2-F-4-NMe$_2$ |
| 3.155 | Na | 2-F-4-NH$_2$ |
| 3.156 | Na | 3,4-Cl$_2$-2-F |
| 3.157 | Na | 3,4,5-Cl$_3$-2-F |
| 3.158 | Na | 2,5-F$_2$-4-OMe |
| 3.159 | Na | 5-Cl-2-F-4-OMe |
| 3.160 | Na | 3-CF$_3$ |
| 3.161 | Na | 2-Cl-3-CF$_3$ |
| 3.162 | Na | 2,4-Cl$_2$-3-CF$_3$ |
| 3.163 | Na | 4-Cl-3-CF$_3$ |
| 3.164 | Na | 5-Cl-3-CF$_3$ |
| 3.165 | Na | 3-CF$_3$-2-F |
| 3.166 | Na | 3-CF$_3$-2,4-F$_2$ |
| 3.167 | Na | 3-CF$_3$-4-F |
| 3.168 | Na | 3-CF$_3$-5-F |
| 3.169 | Na | 4-CF$_3$ |
| 3.170 | Na | 3-Cl-4-CF$_3$ |
| 3.171 | Na | 3,5-Cl$_2$-4CF$_3$ |
| 3.172 | Na | 5-Cl-4-CF$_3$ |
| 3.173 | Na | 4-SMe |
| 3.174 | Na | 3-Cl-4-SMe |
| 3.175 | Na | 5-Cl-4-SMe |
| 3.176 | Na | 3,5-Cl$_2$-4-SMe |
| 3.177 | Na | 3-F-4-SMe |
| 3.178 | Na | 3,5-F$_2$-4-SMe |
| 3.179 | Na | 5-F-4-SMe |
| 3.180 | Na | 3-Cl-5-F-4-SMe |
| 3.181 | K | — |
| 3.182 | K | 3-Cl |
| 3.183 | K | 3,4-Cl$_2$ |
| 3.184 | K | 3,4,5-Cl$_3$ |
| 3.185 | K | 3,5-Cl$_2$ |
| 3.186 | K | 3,5-Cl$_2$-4-OMe |
| 3.187 | K | 3,5-Cl$_2$-4-F |
| 3.188 | K | 2,4-Cl$_2$ |
| 3.189 | K | 2,3,4-Cl$_3$ |
| 3.190 | K | 2,4-Cl$_2$-3-F |
| 3.191 | K | 2,4-Cl$_2$-3-OMe |
| 3.192 | K | 2,4-Cl$_2$-3-Me |
| 3.193 | K | 2,4,5-Cl$_3$ |
| 3.194 | K | 2-Cl-4-F |
| 3.195 | K | 2-Cl-4-OMe |

TABLE 3-continued

Inventive compounds of the formula (I) wherein $R^1$ and $R^4$ are each hydrogen, $R^3$ is fluorine, and $R^2$ and $R^5$ ave the meanings given in Table 1

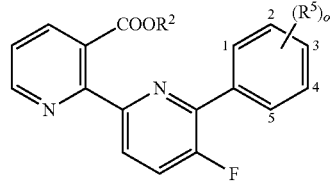

| Ex. No. | $R^2$ | $R^5$ |
|---|---|---|
| 3.196 | K | 2-Cl-4-Me |
| 3.197 | K | 3-F |
| 3.198 | K | 4-Cl-3-F |
| 3.199 | K | 3,4-$F_2$ |
| 3.200 | K | 3,4,5-$F_3$ |
| 3.201 | K | 3,5-$F_2$-4-Me |
| 3.202 | K | 3,5-$F_2$-4-OMe |
| 3.203 | K | 2,4-$F_2$ |
| 3.204 | K | 3-Cl-4-F |
| 3.205 | K | 2,4-$F_2$-3-OMe |
| 3.206 | K | 2-F-4-OMe |
| 3.207 | K | 4-Cl-2-F |
| 3.208 | K | 2,3,5-$F_3$ |
| 3.209 | K | 5-Cl-2,3-$F_2$ |
| 3.210 | K | 2-F-4-Me |
| 3.211 | K | 5-Cl-3-F-4-OMe |
| 3.212 | K | 3,5-$F_2$-4-$NMe_2$ |
| 3.213 | K | 5-Cl-3-F-4-$NMe_2$ |
| 3.214 | K | 2-F-4-$NMe_2$ |
| 3.215 | K | 2-F-4-$NH_2$ |
| 3.216 | K | 3,4-$Cl_2$-2-F |
| 3.217 | K | 3,4,5-$Cl_3$-2-F |
| 3.218 | K | 2,5-$F_2$-4-OMe |
| 3.219 | K | 5-Cl-2-F-4-OMe |
| 3.220 | K | 3-$CF_3$ |
| 3.221 | K | 2-Cl-3-$CF_3$ |
| 3.222 | K | 2,4-$Cl_2$-3-$CF_3$ |
| 3.223 | K | 4-Cl-3-$CF_3$ |
| 3.224 | K | 5-Cl-3-$CF_3$ |
| 3.225 | K | 3-$CF_3$-2-F |
| 3.226 | K | 3-$CF_3$-2,4-$F_2$ |
| 3.227 | K | 3-$CF_3$-4-F |
| 3.228 | K | 3-$CF_3$-5-F |
| 3.229 | K | 4-$CF_3$ |
| 3.230 | K | 3-Cl-4-$CF_3$ |
| 3.231 | K | 3,5-$Cl_2$-4$CF_3$ |
| 3.232 | K | 5-Cl-4-$CF_3$ |
| 3.233 | K | 4-SMe |
| 3.234 | K | 3-Cl-4-SMe |
| 3.235 | K | 5-Cl-4-SMe |
| 3.236 | K | 3,5-$Cl_2$-4-SMe |
| 3.237 | K | 3-F-4-SMe |
| 3.238 | K | 3,5-$F_2$-4-SMe |
| 3.239 | K | 5-F-4-SMe |
| 3.240 | K | 3-Cl-5-F-4-SMe |

B. Formulation Examples a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
 75 parts by weight of a compound of the formula (I) and/or salts thereof,
 10 parts by weight of calcium lignosulfonate,
 5 parts by weight of sodium laurylsulfate,
 3 parts by weight of polyvinyl alcohol and
 7 parts by weight of kaolin,
 grinding the mixture in a pinned-disk mill, and granulating the powder in a fluidized bed by spray application of water as a granulating liquid.

f) Water-dispersible granules are also obtained by homogenizing and precomminuting
 25 parts by weight of a compound of the formula (I) and/or salts thereof,
 5 parts by weight of sodium 2,2'-dinaphthylmethane-6,6'-disulfonate,
 2 parts by weight of sodium oleoylmethyltaurate,
 1 part by weight of polyvinyl alcohol,
 17 parts by weight of calcium carbonate and
 50 parts by weight of water,
 then grinding the mixture in a bead mill and atomizing and drying the resulting suspension in a spray tower by means of a one-phase nozzle.

C. Biological Examples

1. Pre-Emergence Herbicidal Action Against Harmful Plants

Seeds of monocotyledonous and dicotyledonous weed plants and crop plants are laid out in sandy loam in wood-fiber pots and covered with soil. The inventive compounds, formulated in the form of wettable powders (WP) or as emulsion concentrates (EC), are then applied to the surface of the soil cover in the form of an aqueous suspension or emulsion at a water application rate equating to 600 to 800 l/ha, with addition of 0.2% wetting agent. After the treatment, the pots are placed in the greenhouse and kept under good growth conditions for the test plants. The damage to the test plants is assessed visually after a test period of 3 weeks by comparison with untreated controls (herbicidal activity in percent (%): 100% activity=the plants have died, 0% activity=like control plants). For example, compounds No. 1.002, 1.182 and 1.242 each show, at an application rate of 1280 g/ha, at least 90% activity against *Viola tricolor* and *Amaranthus retroflexus*.

2. Post-Emergence Herbicidal Action Against Harmful Plants

Seeds of monocotyledonous and dicotyledonous weed and crop plants are laid out in sandy loam in wood-fiber pots, covered with soil and cultivated in a greenhouse under good growth conditions. two to three weeks after sowing, the test plants are treated at the one-leaf stage. The inventive compounds, formulated in the form of wettable powders (WP) or as emulsion concentrates (EC), are then sprayed as aqueous suspension or emulsion at a water application rate equaling to 600 to 800 l/ha with the addition of 0.2% of wetting agent onto the green parts of the plants. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). For example, compounds No. 1.002, 1.241, 1.182 and 1.242 each show, at an application rate of 320 g/ha, at least 80% activity against *Amaranthus retroflexus*.

The invention claimed is:

1. A 6-phenyl-2,2'-bipyridine-3-carboxylic acid derivative of formula (I), and/or an N-oxide and/or a salt thereof

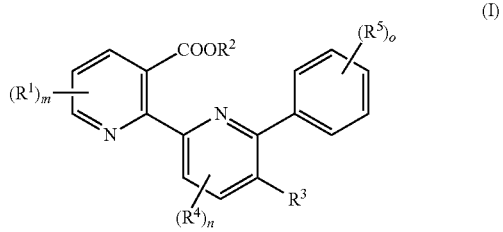

(I)

in which
R$^1$, R$^4$, and R$^5$ independently of one another are nitro, halogen, cyano, formyl, (C$_1$-C$_6$)-alkyl, halo(C$_1$-C$_6$)-alkyl, N(R$^7$)$_2$, OR$^7$, or OCOR$^7$,
R$^2$ is hydrogen, (C$_1$-C$_6$)-alkyl, or halo-(C$_1$-C$_6$)-alkyl,
R$^3$ is hydrogen or halogen,
R$^7$ is hydrogen, (C$_1$-C$_6$)-alkyl, or (C$_1$-C$_6$)-haloalkyl,
n is 0, 1 or 2,
m is 0, 1, 2 or 3, and
o is 0, 1, 2, 3, 4 or 5.

2. A 6-phenyl-2,2'-bipyridine-3-carboxylic acid derivative and/or an N-oxide and/or a salt thereof as claimed in claim 1, in which
R$^1$, R$^4$, and R$^5$ independently of one another are nitro, halogen, cyano, formyl, (C$_1$-C$_6$)-alkyl, halo-(C$_1$-C$_6$)-alkyl, N(R$^7$)$_2$, or OR$^7$,
R$^2$ is hydrogen, (C$_1$-C$_6$)-alkyl, or halo-(C$_1$-C$_6$)-alkyl,
R$^3$ is hydrogen or halogen,
R$^7$ is hydrogen or (C$_1$-C$_6$)-alkyl,
n is 0 or 1,
m is 0, 1, 2, and
o is 0, 1, 2, or 3.

3. A 6-phenyl-2,2'-bipyridine-3-carboxylic acid derivative and/or an N-oxide and/or a salt thereof as claimed in claim 1, in which
R$^1$, R$^4$, and R$^5$ independently of one another are in each case nitro, halogen, cyano, formyl, (C$_1$-C$_4$)-alkyl, halo-(C$_1$-C$_4$)-alkyl, N(R$^7$)$_2$, or OR$^7$,
R$^2$ is hydrogen or (C$_1$-C$_6$)-alkyl,
R$^3$ is hydrogen, halogen, (C$_1$-C$_6$)-alkyl or halo-(C$_1$-C$_6$)-alkyl,
R$^7$ is hydrogen or (C$_1$-C$_6$)-alkyl,
n is 0 or 1,
m is 0 or 1, and
o is 0, 1, 2 or 3.

4. A herbicidal composition comprising a herbicidally active content of at least one compound of formula (I) and/or an N-oxide and/or a salt thereof as claimed in claim 1 and one or more formulation auxiliaries.

5. A method for controlling unwanted plants, comprising applying an effective amount of at least one compound of formula (I) and/or an N-oxide and/or a salt thereof as claimed in claim 1 to one or more plants and/or to a site of unwanted vegetation.

6. The method as claimed in claim 5, wherein the compound of formula (I) and/or an N-oxide and/or a salt thereof is used for controlling one or more unwanted plants in one or more crops of one or more useful plants.

7. The method as claimed in claim 6, wherein the useful plants are one or more transgenic useful plants.

8. A 6-phenyl-2,2'-bipyridine-3-carboxylic acid derivative as claimed in claim 1 having the formula

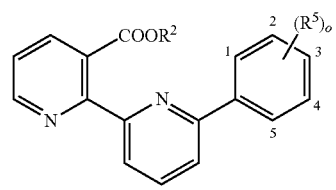

in which R$^2$ is methyl and (R$^5$)$_o$ is 3-chloro.

9. A 6-phenyl-2,2'-bipyridine-3-carboxylic acid derivative as claimed in claim 1 having the formula

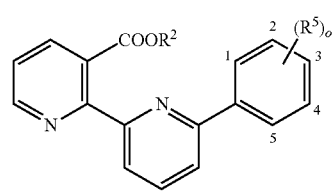

in which R$^2$ is potassium and (R$^5$)$_o$ is 3-chloro.

10. A 6-phenyl-2,2'-bipyridine-3-carboxylic acid derivative as claimed in claim 1 having the formula

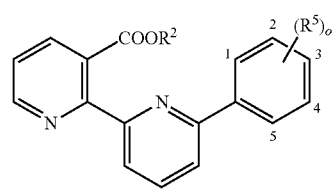

in which R$^2$ is methyl and (R$^5$)$_o$ is 3-chloro-5-fluoro.

11. A 6-phenyl-2,2'-bipyridine-3-carboxylic acid derivative as claimed in claim 1 having the formula

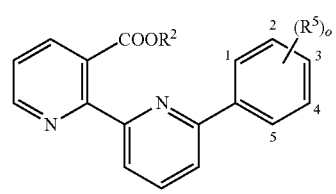

in which R$^2$ is potassium and (R$^5$)$_o$ is 3-chloro-5-fluoro.

* * * * *